United States Patent
Rector

[11] Patent Number: 5,901,424
[45] Date of Patent: May 11, 1999

[54] TROCAR BUTTON

[76] Inventor: Charles W. Rector, 3304 Russel Rd., Cenralia, Wash. 98531

[21] Appl. No.: 08/864,843

[22] Filed: May 29, 1997

[51] Int. Cl.$^6$ ...................................................... A01N 1/00
[52] U.S. Cl. ........................... 27/21.1; 81/461; 411/405; 411/404; 411/908; 606/108; 606/185
[58] Field of Search .............................. 27/21.1; 606/185, 606/108; 411/395, 403, 407, 408, 426, 404, 405, 908

[56] References Cited

U.S. PATENT DOCUMENTS

| | | | |
|---|---|---|---|
| 2,437,381 | 3/1948 | Cullen | 27/21.1 |
| 3,103,052 | 9/1963 | Rector . | |
| 3,195,215 | 7/1965 | Rector . | |
| 3,421,190 | 1/1969 | Rector . | |
| 3,465,398 | 9/1969 | Rector | 27/21.1 |
| 3,507,017 | 4/1970 | Rector | 27/21.1 |
| 4,240,186 | 12/1980 | Rector . | |

Primary Examiner—Michael Powell Buiz
Assistant Examiner—David O. Reip

[57] ABSTRACT

There is provided a trocar button having an enlarged flat head at the larger exterior end connecting with a conical body and a pointed bulbous end. The large part of the conical body connects with the enlarged flat head. Between the small part of the conical body and the pointed bulbous end there is a neck. In the body of the trocar button including the enlarged flat head, the conical body, the neck, and part of the pointed bulbous end, there is a cavity. With the removal of the pointed bulbous end at the neck, there is created a through passageway in the trocar button. A needle attached to a syringe, can be inserted in the through passageway and into the interior of the cadaver. Then, an embalming fluid can be forced through the needle and into the interior of the cadaver. Also, the through passageway allows gas in the cadaver to escape. Further, if there be a liquid in the cadaver some of that liquid can collect in the passageway. On the exterior of the conical body there is a thread. In the head of the trocar button there is a receiving area for receiving a tool for assisting in screwing the trocar button into the aperture in the cadaver or for removing the trocar button from the aperture in the cadaver.

11 Claims, 4 Drawing Sheets

TROCAR BUTTON

CROSS-REFERENCES TO RELATED PATENT APPLICATIONS (IF ANY)

The applicant has three patents and one pending patent application identified as follows:

U.S. Pat. No. 3,103,052, issuing date of Sep. 10, 1963, entitled "NATURAL EXPRESSION FORMER";

U.S. Pat. No. 3,195,215, issuing date of Jul. 20, 1965, entitled "NATURAL EXPRESSION FORMER WITH BITE INDENTATION";

U.S. Pat. No. 4,240,186, issuing date of Dec. 23, 1980, entitled "FRENUM LOCK"; and Ser. No. 08/745,742, filing date of Nov. 12, 1996 entitled "A FRENUM LOCK".

There are two Canadian patents identified as follows:

741,953, issuing date of Sep. 6, 1996, entitled "NATURAL EXPRESSION FORMER"; and 779,003, issuing date of Feb. 27, 1968, entitled, "TROCAR BUTTON".

STATEMENT AS TO RIGHTS TO INVENTIONS MADE UNDER FEDERALLY SPONSORED RESEARCH AND DEVELOPMENT (IF ANY)

The applicant developed the subject invention with private finances and there was no federally sponsored research and development.

BACKGROUND OF THE INVENTION

1. Field of the Invention

In the preparation of cadaver for burial, it is often necessary to seal an aperture in the cadaver. There may have been an accident whereby a stick, a rod, or glass may have caused an aperture in a human being, and this aperture remains in the cadave. Further, a knife wound or a bullet hole may have caused an aperture in a human being and this aperture remains with the cadaver It is often necessary to seal such an aperture Further, with the cadaver there may be a deliberate opening or deliberate openings to introduce embalming fluid and also to vent gases from the interior of the cadaver.

2. Description of the Prior Art

A trocar in surgery is a sharp pointed instrument enclosed in a cannula used for withdrawing fluid from a cavity such as food from the abdominal cavity.

A cannula in surgical technology is a tube for insertion into the body and used to draw fluid or to introduce medication Cullen, U.S. Pat. No. 2,437,381, is directed to an embalming device. Cullen teaches of a trocar button for use in closing an aperture made in the body for the purpose of aspirating body fluids and/or for the introduction of embalming fluid. There is a head 2 of generally disc-like shape. There is a body 4 of truncated conical contour tapering downwardly from its junction with the head to the free end or tip 5.

There are two recesses 2a in the head 2 for receiving the parallel pins 8 of a tool 9.

The body portion of the trocar button is of a generally frustum of a cone having on the outside surface threads 8 to assist in screwing the trocar into the aperture in the cadaver.

There is no through passageway in Cullen for introducing embalming fluid into the cadaver. In effect, Cullen's embalming device is a plug to plug a hole or aperture in a cadaver so as to prevent the escape of gases and fluids from the cadaver.

Rector, U.S. Pat. No. 3,465,398, teaches of a trocar button having a conical body 1 connecting with the enlarged flat head 2 On the outside of the conical body 1 there are threads 3 to assist in screwing the trocar button into the aperture in the cadaver.

Rector teaches of a bulbous head 4 on the small end of the conical body 1.

There is a channel 7 in the trocar button which allows a needle to be positioned in the button. There is a neck 5 between the end of the conical body 1 and the bulbous end 4. A channel 7 connects with the enlarged head 2 and also with the bulbous member 4. or the tip 4 The trocar button of Rector can be used for plugging an aperture in a cadaver to prevent the loss of fluid and gas. Or, the tip 4 can be severed from the conical body at the neck 5 to expose the channel 7 The channel 7 along with a cavity 6 provides a through passageway in the trocar button for the insertion of a needle for inserting embalming fluid into the cadaver or for the removal of material inside of the fabric. Also, the through passageway 7 and the cavity 6 make it possible for liquid and gas to escape from the cadaver The liquid which escapes will remain in the channel 7 and/or the cavity 6.

Again, a needle connected to syringe can be inserted in the cavity 6 and the channel 7 for introducing embalming fluid and the like into the cadaver. The needle is positioned in the cavity 6 and the channel 7.

SUMMARY OF THE INVENTION

The trocar button serves many purposes One of the purposes is a positive seal of a aperture in the cadaver. Another purpose is to allow liquid and gas to escape from the cadaver. In a cadaver there may be a build-up of gas. With this subject trocar button and a through passageway in the trocar button, the gas can escape from the interior of the cadaver. Further, there may be a increase in liquid in the cadaver and the pressure in the cadaver forces the liquid through the passageway in the trocar button and into the cavity area of the trocar button. Also, with the through passageway in the trocar button there is the possibility of inserting a needle through the passageway in the trocar button. The needle connects with a source of embalming fluid The embalming fluid can be forced into the interior of the cadaver and through the aperture for preservation purposes.

The trocar button comprises a large head connecting with a conical body The large end of the conical body connects with the enlarged head. The small end of the conical body connects with a bulbous end having a point for ease of insertion of the trocar button into the aperture The connection between the small end of the conical body and the bulbous end is referred to as a neck.

There is a cavity in the trocar button. The cavity extends into a passageway or a channel in the small end. of the conical body, in the neck, and even into the bulbous end. It is possible to sever the bulbous end, at the neck, from the end of the conical body. This results in the formation of a through passageway in the trocar button. The through passageway allows a needle connected to a syringe to introduce embalming fluid into the cadaver or to remove fluid from the cadaver for sampling purposes.

On the outside of the conical body there are threads or conical threads.

In the enlarged end or enlarged head of the trocar button, there are four recesses. The recesses are at 90 degree angles to each other and appear to be in the form of a cross.

That part of the cavity in said head of the trocar button comprises a first set of two spaced-apart opposed walls defining a first groove which extends into the conical body. A first distance, in said first set, between said two opposed walls and the head being less than the distance between said two opposed walls in the conical body so that said two opposed walls and the head are able to grip a tool. That part of the cavity in the head comprises a second set of two spaced-apart opposed walls defining a second groove which extends into the conical body The distance, in said second set, between said two opposed walls and the head being less than the distance between said two opposed walls in the conical body so that said two opposed walls and the head are able to grip a tool.

A tool having a projection or extension means can be positioned in the first set of two spaced-apart opposed walls and in the second set of two spaced-apart opposed walls so that the first and second set can grip the projected means on the end of the tool. This allows a person to screw the trocar button into the aperture in the cadaver.

OBJECTS AND ADVANTAGES

An object of this invention is to provide a trocar button having a pointed end for ease of insertion of a button into an aperture in the cadaver or for ease of screwing the trocar button into an aperture in the cadaver.

Another object is to provide an opening groove in the exposed end or exposed head of the trocar button in which opening the groove is narrower than the continuing groove in the body of the trocar button so that a tool can be positioned in the opening groove and be held in position by a squeezed grip of the opposed walls in the opening groove in the head of the trocar button.

Another object and advantage of this invention is to provide thinner walls in the trocar button than have been provided in previous similar devices so that there is a larger cavity in the body of the trocar button for retention of body fluid flowing from the cadaver into the trocar button.

An additional important object is to provide a unitary trocar button which can be easily handled and manipulated by a person working with a cadaver.

An additional important object is to provide a trocar button with thinner walls than have been provided in other similar devices so that less material is used in making the trocar button and therefore there is a less expensive trocar button.

Additional objects, advantages and novel features of the invention will be set forth in part in the description which follows, and in part will become apparent to those skilled in the art upon examination of the following or may be learned by the practice of the invention The objects and advantages of the invention may be realized and attained by means of the instrumentalities and combinations particularly pointed out in the appended claims.

DESCRIPTION OF THE PREFERRED EMBODIMENT(S)

Figure 1:
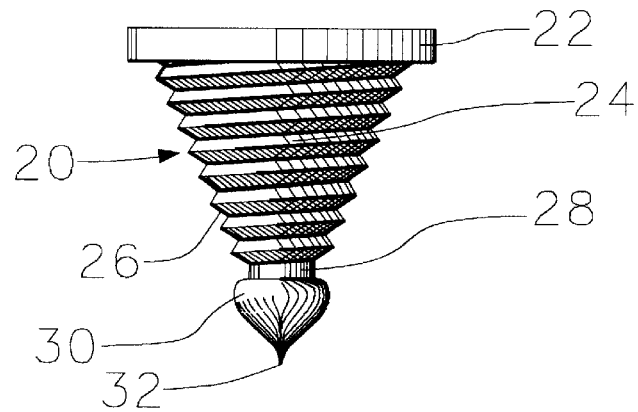
FIG. 1 is a side elevational view of the trocar button.
Figure 2:
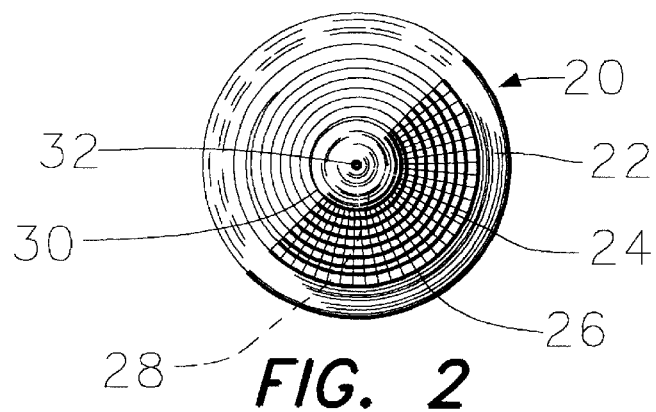
FIG. 2 is a bottom plan view of the trocar button.

There is a trocar button 20 having a circular head 22 There is a conical body 24 connecting with the head 22. The conical body 24 is in the configuration of a frustum of a cone The diameter of the body 24 is less than the diameter of the head 22.

On the outside surface of the conical body 24 there are threads 26.

Connecting with the smaller part of the conical body 24, and away from the head 22, is a cylindrical body 28. The cylindrical body 28 is of a smaller diameter than the diameter of the conical body 24.

There connects with the outer part of the cylindrical body 28 a bulbous end. The diameter of the bulbous end 30 is larger than the diameter of the cylindrical body 28.

On the outer end of the bulbous end 30 there is a pointed end 32. In the head 22 there is a recess 38.

Figure 3:
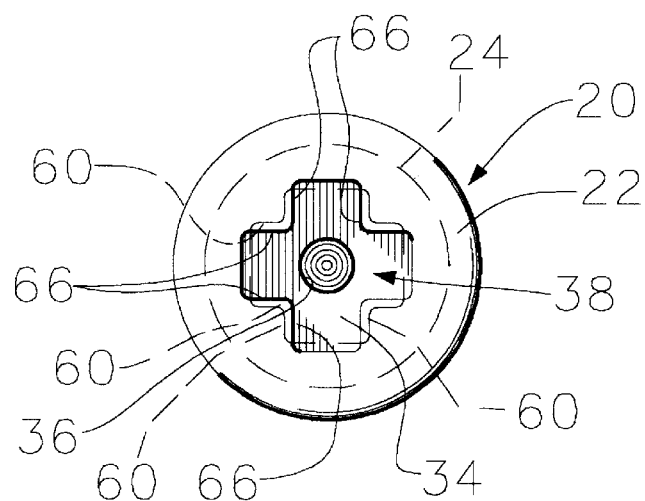
FIG. 3 is a top plan view of the trocar button.

In FIG. 3 it is seen that the recess 38 has four enlarged portions 34 at right angles to each other so as to present the configuration of a cross.

In the central portion of the recess 38 and also in the conical body 24 and the bulbous end 30 there is a recess 36.

Figure 6:
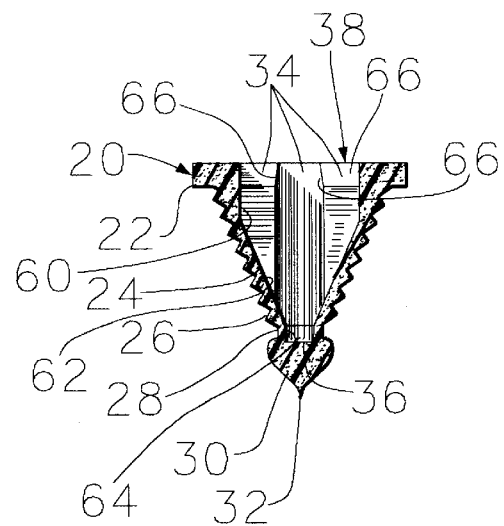
FIG. 6 is a longitudinal fragmentary side elevational view of one-half of a trocar button and illustrating the large cavity in the trocar button and that part of the cavity in said of the trocar button comprising a first set of two spaced-apart opposed walls defining a first groove which extends into the conical body and also the distance, in said first set, between said two opposed walls and the head being less than the distance between said two opposed walls and the conical body so that said two opposed walls and the head are able to grip said tool.

In FIG. 6 there is seen the recess 36 which extends through the cylindrical body 28 and into the upper part of the bulbous end 30.

Figure 8:
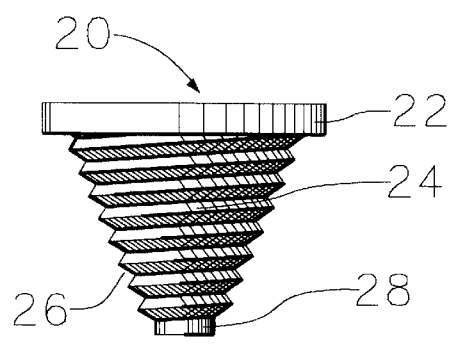
FIG. 8 is a side elevational view of the trocar button with the pointed bulbous end removed so as to have a through passageway in the trocar button for acceptance of a needle on the end of a syringe.

The bulbous end 30 can be separated from the conical body 24 by means of a sharp knife or a pair of scissors. The result is the trocar button illustrated in FIGS. 8 and 9 with the passageway 36 being a through passageway in the conical body 24, the circular head 22, and the remainder of the cylindrical body 28.

The passageway 36 can receive a hypodermic needle. The hypodermic needle may be used for injecting embalming fluid into the cadaver or may be used for withdrawing fluid, such as liquid and a gas, from the cadaver.

Figure 9:
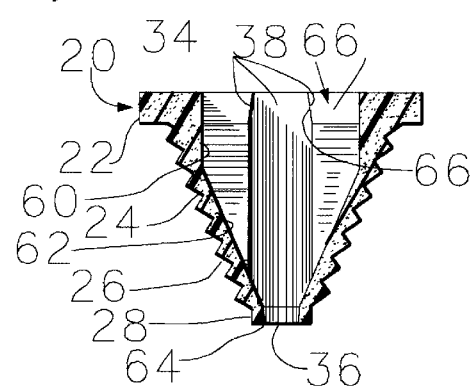
FIG. 9 is a sectional elevational view of a half of a trocar button, longitudinally cut on lines 9—9 of FIG. 8, and with the pointed bulbous end removed so as to show the through passageway in the trocar button.

In FIG. 9, a longitudinal cross-sectional view of the trocar button 20, it is seen that the recess 38 near the head 22 has a straight upper wall 60. Then, the straight upper wall 60 angles inwardly in the conical body 24 to form a sloping wall 62 Then, the sloping wall 62 meets with a straight wall 64 in the cylindrical body 28. In FIG. 9 it is seen that there is a large void in the trocar button 20. This void is defined by the recess 38, the four enlargements 34, and the passageway 36 in the cylindrical body 28. As a result, less material is required for making the subject trocar button in relation to the trocar buttons of Cullen and W Rector.

Further, the cavity defined by 38, 34, 36, 60, 62, 64, and 66 is a larger cavity than the cavity defined by Cullen or W. Rector. The cadaver may give off some fluids such as a gas or may give off some fluids such as a liquid. The gas can pass through the passageway 36 and past the straight wall 64, the sloping wall 62, the straight upper wall 60, and the enlargements 34 so as to escape from the cadaver. The trocar button in this instance is a safety valve for allowing gas and/or liquid generated in the cadaver to escape from the cadaver.

Also, the cadaver may generate some liquid and the trocar button allows the liquid to pass through the passageway 36 and into the interior of the conical body 24. Then, the liquid in the trocar button 20 can be removed by means of a syringe or the liquid may flow back into the body of the cadaver.

Figure 4:
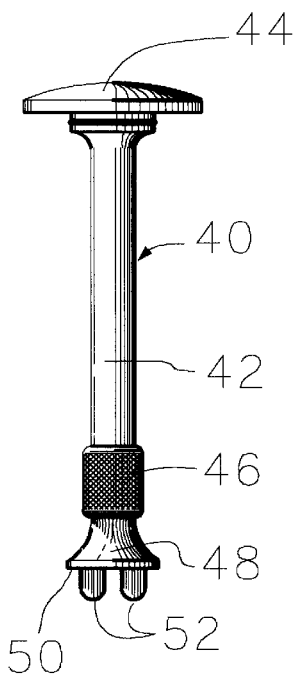
FIG. 4 is a side elevational view of a tool for use in inserting and also for use in removing a trocar button from a cadaver.

In FIG. 4 there is illustrated a tool 40 having a cylindrical body stem 42, a rotatable palm engaging disk 44 at the upper end of the stem 42. On the lower end of the stem 42 there is a knurled portion 46 so as to allow a person to grab the knurled portion and rotate the tool 40.

The knurled portion 46 flares outwardly at 48 to form a flared end 48. The flared end 48 has a bottom surface 50. Two pins 52 project outwardly from the bottom surface 50.

Figure 5:
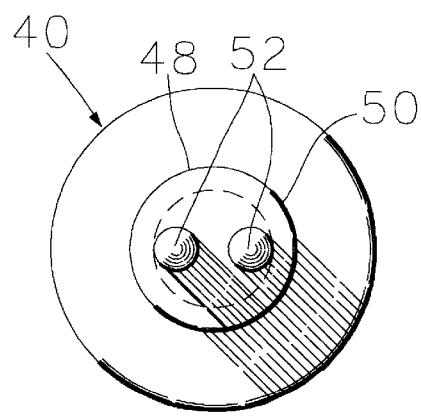
FIG. 5 is a bottom plan view of said tool.

In FIG. 5 there is illustrated a bottom plan view of the tool 40 and this view illustrates the two pins 52 on the outer bottom surface 50.

Figure 7:
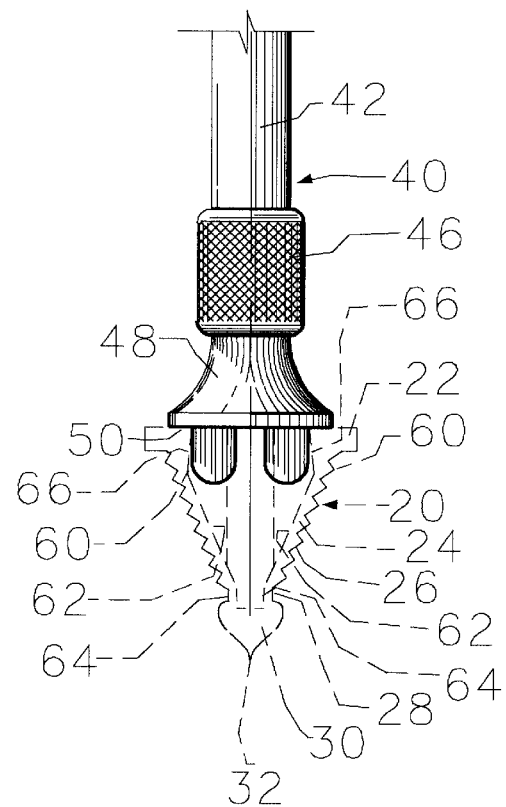
FIG. 7 illustrates, in phantom, the trocar button, and also the iv tool being applied to the trocar button (see Cullen, FIG. 3)

In FIG. 7 there is illustrated the tool 40 being positioned next to the trocar button 20 and with the two prongs 52 directed inwardly and between the walls 66 of the enlargements 34. It is possible for a worker to grab the rotatable palm engaging disk 44 and rotate the trocar button 20. The trocar button, with the pointed end 32 on the end of the bulbous end 30 can be started in the aperture in the cadaver. Then, the tool 40 can be positioned in the trocar button with the pins 52 projecting inwardly into the enlargements 34. The rotatable palm engaging disk 44 can be rotated so as to screw the trocar button 20 into the aperture in the cadaver. Alternatively, the person can grip the knurled portion 46 between the finger and the thumb and rotate the tool 40 to screw the trocar button 20 into the aperture in the cadaver.

Or, the prongs 52 of the tool 40 can be inserted between the walls 66 and between the walls 60 of the trocar button 20. Then, the button 20 on the end of the tool 40 can be screwed into the aperture in the cadaver.

In FIG. 6 it is seen that the passageway 36 extends into the upper part of the bulbous end 30 With the cutting of the trocar button at the cylindrical body 28, it is ensured that the passageway 36 will extend all the way through the head 22, the conical body 24, and the cylindrical body 28.

With reference to FIG.S 3, 6, 7, and 9 it is seen that the upper part of the straight upper wall 60 converges inwardly at 66. The convergence inwardly of the upper part of the wall 60 at 66 narrows the opening to the enlargement 34. The distance between the opposed converging walls 66 at the entrance to 34 is less than the diameter of the pin 52. As a result, the pin 52 in the tool 40 must be pressed into the opposed converging walls 66 and into the straight upper wall 60 as illustrated in FIG. 7. As a result, the trocar button 20 is securely fastened to and positioned on the two spaced-apart pins 52 on the bottom surface 50 of the tool 40.

The upper conversence of the opposed walls 66 of the straight upper wall 60 makes it possible to firmly position the trocar button 20 on the tool 40 for ease of manipulation and screwing of the trocar button 40 into an aperture in the cadaver.

The enlargements 34 are in essence a cavity in said head 22, said conical body 24, said cylindrical body 28, and said bulbous end 30. That part of the cavity in said head comprising a first set of two spaced-apart opposed walls defining a first groove which extends into the conical body. There is a first distance, in said first set, between said two opposed walls 66 in the head 22 being less than the distance between said two opposed walls 60 in the conical body 24 so that said two opposed walls 66 in the head are able to grip the pins 52 on the end of the tool 40. Also, that part of the cavity in said head 22 comprises a second set of two spaced-apart opposed walls 66 defining a second groove which extends into the conical body 24. A second distance, in said second set, between said two opposed walls 66 and the head 22 being less than the distance between said two opposed walls 60 in the conical body so that said two opposed walls in the head are able to grip the pins 52 on the tool 40.

The materials to construct the trocar button 20 can be many. It is conceivable that the trocar button can be made of a metal such as aluminum or other metals such as magnesium or beryllium. Also, the trocar button can be made of a plastic. There are many available suitable plastics and the trocar button 20 can be injected molded from a plastic. The trocar button can be a unitary one-piece plastic.

In FIG. 7 it is seen that the tool 40 is positioned so that the outer surface 50 is bearing against the outer surface of the head 22. The prongs 52 are positioned in two of the enlargements in the head 22. In this way the disk 44 or the knurled portion 46 can be rotated to screw the trocar button 20 into the aperture in the cadaver.

Figure 10:
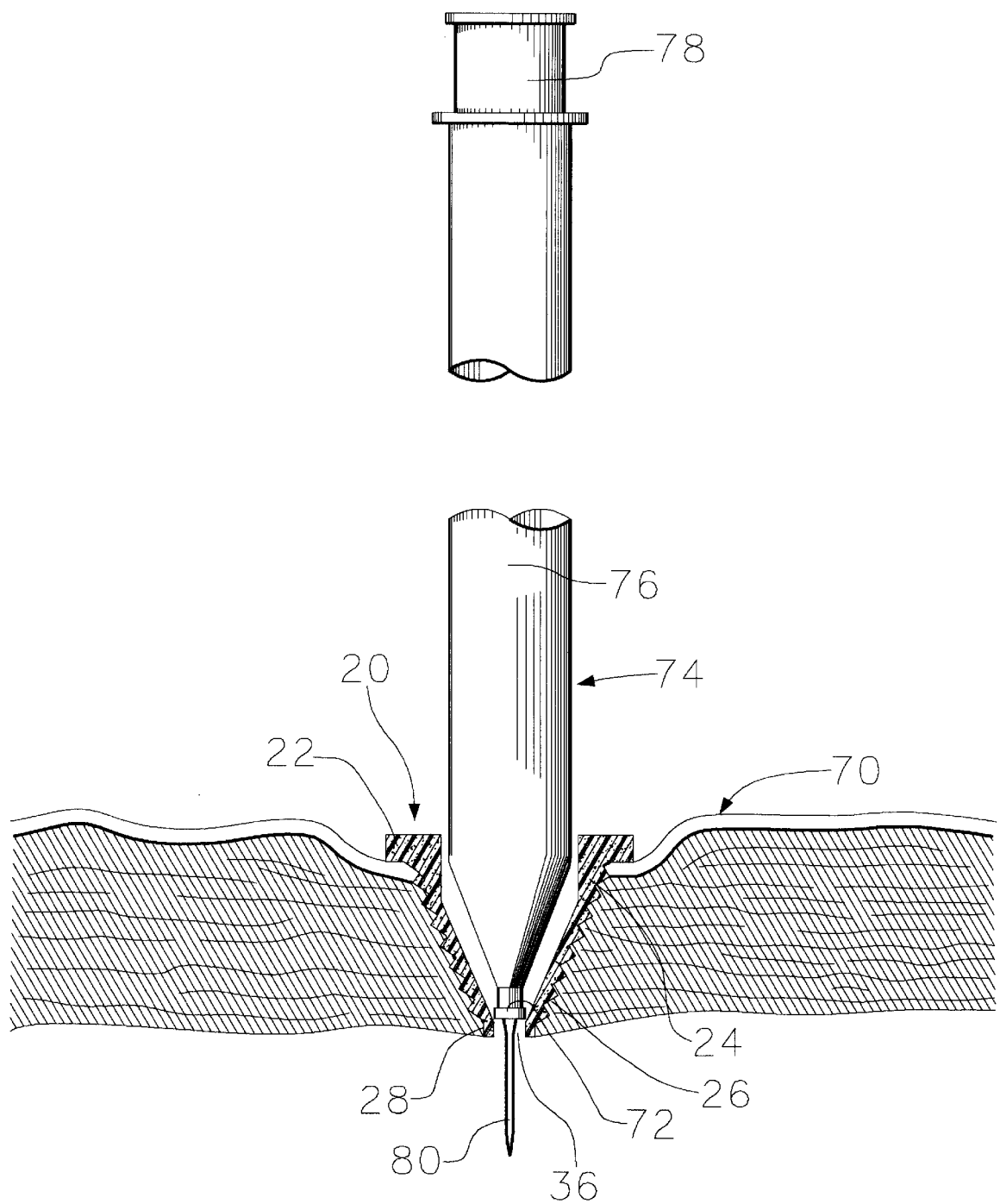
FIG. 10 is a fragmentary illustration of a cadaver with an aperture and a trocar button in the aperture and a syringe in the trocar button with a needle on the syringe and inside of the cadaver

With respect to FIG. 10 it is seen that there is a partial showing of a cadaver 70 having an aperture 72.

A trocar button 20 is positioned in the aperture 72. The trocar button 20 comprises a cylindrical body 28, a conical body 24, and the threads 26. There is a passageway 36 to the trocar button 20.

The bulbous end 30 and the pointed end 32 have been removed from the trocar button 20 to make available the passageway 36.

A syringe 74 can be positioned in the interior of the trocar button 20. The syringe 74 has a barrel 76 There is a plunger 78 in the barrel 76.

On the end of the syringe 74 there is a hypodermic needle 80 projecting through the passageway 36 in the cylindrical body 28.

With the syringe 74 it is possible to inject embalming fluid into the cadaver 70.

With the syringe 74 it is possible to remove liquid, and even gas, from the cadaver 70.

The reader is to understand that the trocar button 20, as illustrated in FIG. 10, can be used without the syringe 74. If there be a build-up of gas or an increase of gas in the cadaver 70, the gas can escape through the passageway 36 from the interior of the cadaver and through the passageway 36 in the trocar button 20 to the outside of the cadaver.

Also, the trocar button 20 and the aperture 72 allows a build-up of liquid in the cadaver 70 to flow through the passageway 36 and into the interior of the trocar button 20.

A trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; and a first distance, in said first set, between said two opposed walls in the head being less then the distance between said two opposed walls in the conical body so that said two opposed walls in the head are able to grip a tool.

A trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; and a screw thread on the exterior of said conical body.

A trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; that part of the cavity in said head comprising a second set of two spaced apart opposed walls defining a second groove which extends into the conical body; and the distance, in said second set, between said two opposed walls in the head being less than the distance between said two opposed walls in the conical body so that said two opposed walls in the head are able to grip a tool.

A trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; and in said neck the wall is thin between the exterior surface and said cavity to allow easy separation of said bulbous end and said conical body.

A trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; a screw thread on the exterior of said conical body; that part of the cavity in said head comprising a second set of two spaced apart opposed walls defining a second groove which extends into the conical body; a second distance, in said second set, between said two opposed walls in the head being less than the distance between said two opposed walls in the conical body so that said two opposed walls in the head are able to grip a tool; and in said neck the wall is thin between the exterior surface and said cavity to allow easy separation of said bulbous end and said conical body.

A trocar button comprising a head; a conical body connecting with said head; a bulbous end; a neck connecting with said conical body and with said bulbous end and being of a lesser dimension than said bulbous end; the larger part of said conical body connecting with said head; and the outer part of said bulbous end terminating in a point for ease of insertion of said trocar button into an aperture.

A trocar button comprising a head; a conical body connecting with said head; a bulbous end; a neck connecting with said conical body and with said bulbous end and being of a lesser dimension than said bulbous end; the larger part of said conical body connecting with said head; the outer part of said bulbous end terminating in a point for ease of insertion of said trocar button into an aperture; a screw thread on the exterior of said conical body; and in said neck the wall is thin between the exterior surface and said cavity to allow easy separation of said bulbous end and said conical body.

A trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; the distance, in said first set, between said two opposed walls in the head being less then the distance between said two opposed walls in the conical body so that said two opposed walls in the head are able to grip a tool; and the outer part of said bulbous end terminating in point for ease of insertion of said trocar button into an aperture.

A trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; the distance, in said first set, between said two opposed walls in the head being less then the distance between said two opposed walls in the conical body so that said two opposed walls in the head are able to grip a tool; the outer part of said bulbous end terminating in point for ease of insertion of said trocar button into an aperture; a screw thread on the exterior of said conical body; that part of the cavity in said head comprising a second set of two spaced apart opposed walls defining a second groove which extends into the conical body; the distance, in said second set, between said two opposed walls in the head being less than the distance between said two opposed walls in the conical body so that said two opposed walls in the head are able to grip a tool; and in said neck the wall is thin between the exterior surface and said cavity to allow easy separation of said bulbous end and said conical body.

A combination of a cadaver and a trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; and the distance, in said first set, between said two opposed walls in the head being less then the distance between said two opposed walls in the conical body so that said two opposed walls in the head are able to grip a tool; said cadaver comprising an aperture in said cadaver; and said combination comprising said trocar button being positioned in said aperture.

A combination of a cadaver and a trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; and the distance, in said first set, between said two opposed walls in the head being less then the distance between said two opposed walls in the conical body so that said two opposed walls in the head are able to grip a tool; said cadaver comprising an aperture in said cadaver; said combination comprising said trocar button being positioned in said aperture; a screw thread on the exterior of said conical body; that part of the cavity in said head comprising a second set of two spaced apart opposed walls defining a second groove which extends into the conical body; the distance, in said second set, between said two opposed walls in the head being less than the distance between said two opposed walls in the conical body so that said two opposed walls in the head are able to grip a tool; and in said neck the wall is thin between the exterior surface and said cavity to allow easy separation of said bulbous end and said conical body.

A combination of a cadaver and a trocar button and comprising said trocar button comprising a head; a conical body connecting with said head; a bulbous end; a neck connecting with said conical body and with said bulbous end and being of a lesser dimension than said bulbous end; larger part of said conical body connecting with said head; the outer part of said bulbous end terminating in point for ease of insertion of said trocar button into an aperture; said cadaver comprising; an aperture in said cadaver; said combination comprising; and said trocar button being positioned in said aperture.

A combination of a cadaver and a trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; the outer part of said bulbous end terminating in point for ease of insertion of said trocar button into an aperture; said cadaver comprising; an aperture in said cadaver; said combination comprising; said trocar button being positioned in said aperture; a screw thread on the exterior of said conical body; and in said neck the wall is thin between the exterior surface and said cavity to allow easy separation of said bulbous end and said conical body.

A combination of a trocar button and a tool for manipulating the trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; that part of the cavity in said head comprising a second set of two spaced apart opposed walls defining a second groove which extends into the conical body; a second distance, in said second set, between said two opposed walls in the head being less than the distance between said two opposed walls in the conical body so that said two opposed walls in the head are able to grip a tool; said tool comprising; a projection means; the width of said projection means being greater than said first distance necessitating the forcing of said projection means between said two opposed walls in said first set so that said two opposed walls in said head are able to grip said tool; said combination comprising; and said projection means being positioned between said two opposed walls in said first set.

A combination of a trocar button and a tool for manipulating the trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; that part of the cavity in said head comprising a second set of two spaced apart opposed walls defining a second groove which extends into the conical body; a second distance, in said second set, between said two opposed walls in the head being less than the distance between said two opposed walls in the conical body so that said two opposed walls in the head are able to grip a tool; said tool comprising; a projection means; the width of said projection means being greater than said first distance necessitating the forcing of said projection means between said two opposed walls in said first set so that said two opposed walls in said head are able to grip said tool; said combination comprising; said projection means being positioned between said two opposed walls in said first set; a screw thread on the exterior of said conical body; and in said neck the wall is thin between the exterior surface and said cavity to allow easy separation of said bulbous end and said conical body.

A combination of a trocar button and a tool for manipulating the trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; that part of the cavity in said head comprising a second set of two spaced apart opposed walls defining a second groove which extends into the conical body; a second distance, in said second set, between said two opposed walls in the head being less than the distance between said two opposed walls in the conical body so that said two opposed walls in the head are able to grip a tool; the outer part of said bulbous end terminating in point for ease of insertion of said trocar button into an aperture; said tool comprising a projection means; the width of said projection means being greater than said first distance necessitating the forcing of said projection means between said two opposed walls in said first set so that said two opposed walls in said head are able to grip said tool; said combination comprising said projection means being positioned between said two opposed walls in said first set.

A combination of a trocar button and a tool for manipulating the trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; that part of the cavity in said head comprising a second set of two spaced apart opposed walls defining a second groove which extends into the conical body; a second distance, in said second set, between said two opposed walls in the head being less than the distance between said two opposed walls in the conical body so that said two opposed walls in the head are able to grip a tool; the outer part of said bulbous end terminating in point for ease of insertion of said trocar button into an aperture; said tool comprising a projection means; the width of said projection means being greater than said first distance necessitating the forcing of said projection means between said two opposed walls in said first set so that said two opposed walls in said head are able to grip said tool; and said combination comprising said projection means being positioned between said two opposed walls in said first set; a screw thread on the exterior of said conical body; and in said neck the wall is thin between the exterior surface and said cavity to allow easy separation of said bulbous end and said conical body.

A combination of a cadaver, a trocar button and a tool for manipulating the trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; that part of the cavity in said head comprising a second set of two spaced apart opposed walls defining a second groove which extends into the conical body; a second distance, in said second set, between said two opposed walls in the head being less than the distance between said two opposed walls in the conical body so that said two opposed walls in the head are able to grip a tool; said tool comprising a projection means; the width of said projection means being greater than said first distance necessitating the forcing of said projection means between said two opposed walls in said first set so that said two opposed walls in said head are able to grip said tool; said cadaver comprising an aperture in said cadaver; said combination comprising said trocar button being positioned in said aperture and said projection means being positioned between said two opposed walls in said first set; a screw thread on the exterior of said conical body; and in said neck the wall is thin between the exterior surface and said cavity to allow easy separation of said bulbous end and said conical body.

A combination of a cadaver, a trocar button and a tool for manipulating the trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; that part of the cavity in said head comprising a second set of two spaced apart opposed walls defining a second groove which extends into the conical body; a second distance, in said second set, between said two opposed walls in the head being less than the distance between said two opposed walls in the conical body so that said two opposed walls in the head are able to grip a tool; said tool comprising a projection means; the width of said projection means being greater than said first distance necessitating the forcing of said projection means between said two opposed walls in said first set so that said two opposed walls in said head are able to grip said tool; said cadaver comprising an aperture in said cadaver; said combination comprising said trocar button being positioned in said aperture and said projection means being positioned between said two opposed walls in said first set.

A combination of a cadaver, a trocar button and a tool for manipulating the trocar button and comprising said trocar button comprising a head; a conical body connecting with said head; a bulbous end; a neck connecting with said conical body and with said bulbous end and being of a lesser dimension than said bulbous end; the larger part of said conical body connecting with said head; a cavity in said head, said conical body and in said bulbous end; that part of the cavity in said head comprising a first set of two spaced apart opposed walls defining a first groove which extends into the conical body; a first distance, in said first set, between said two opposed walls in the head being less then the distance between said two opposed walls in the conical body so that said two opposed walls in the head are able to grip a tool; that part of the cavity in said head comprising a second set of two spaced apart opposed walls defining a second groove which extends into the conical body; a second distance, in said second set, between said two opposed walls in the head being less than the distance between said two opposed walls in the conical body so that said two opposed walls in the head are able to grip a tool; said tool comprising a projection means; the width of said projection means being greater than said first distance necessitating the forcing of said projection means between said two opposed walls in said first set so that said two opposed walls in said head are able to grip said tool; said cadaver comprising an aperture in said cadaver; said combination comprising said trocar button being positioned in said aperture and said projection means being positioned between said two opposed walls in said first set; a screw thread on the exterior of said conical body; and in said neck the wall is thin between the exterior surface and said cavity to allow easy separation of said bulbous end and said conical body.

1997 Charles W. Rector

A portion of the disclosure of this patent document contains material which is subject to copyright protection The copyright owner has no objection to the facsimile reproduction by anyone of the patent document or the patent disclosure, as it appears in the Patent and Trademark Office patent file or records, but otherwise reserves all copyright rights whatsoever.

What I claim is:

1. A trocar button comprising:

a head;

a conical body connecting with said head and said conical body having a larger part, a smaller part; and an outside surface a bulbous end;

a neck connecting with said conical body and with said bulbous end and being of a lesser dimension than said bulbous end and said neck having an exterior surface;

said larger part of said conical body connecting with said head;

a cavity in said head, said conical body and in said bulbous end;

part of said cavity in said head comprising a first set of two spaced apart opposed walls defining a first groove which extends into the conical body; and a first distance, in said first set, between said two spaced apart opposed walls in the head being less than the distance between said two opposed walls in the conical body so that said two opposed walls in the head are able to grip a tool.

2. A trocar button according to claim 1 and comprising:
a screw thread on the outside surface of said conical body.

3. A trocar button according to claim 1 and comprising:
part of said cavity in said head comprising a second set of two spaced apart opposed walls defining a second groove which extends into the conical body; and in said second set, the distance between said two opposed walls in the head being less than the distance between said two opposed walls in the conical body so that said two opposed walls in the head are able to grip a tool.

4. A trocar button according to claim 1 and comprising:
said neck housing part of said cavity and a wall between said exterior surface and said cavity; and in said neck said wall is thin between said exterior surface and said cavity to allow easy separation of said bulbous end and said conical body.

5. A trocar button according to claim 1 and comprising:

a screw thread on the outside surface of said conical body;

that part of the cavity in said head comprising a second set of two spaced apart opposed walls defining a second groove which extends into the conical body;

a second distance, in said second set, between said two opposed walls in the head being less than the distance between said two opposed walls in the conical body so that said two opposed walls in the head are able to grip a tool;

said neck housing part of said cavity and a wall between said exterior surface and said cavity;

in said neck said wall is thin between said exterior surface and said cavity to allow easy separation of said bulbous end and said conical body.

6. A trocar button comprising:

a head;

a conical body connecting with said head and said conical body having a larger part, and a smaller part, and outside surface a bulbous end;

a neck connecting with said conical body and with said bulbous end and being of a lesser dimension than said bulbous end;

said larger part of said conical body connecting with said head;

a cavity in said head, said conical body and in said bulbous end;

part of said cavity in said head comprising a first set of two spaced apart opposed walls defining a first groove which extends into the conical body;

in said first set, the distance between said two opposed walls in the head being less than the distance between said two opposed walls in the conical body so that said two opposed walls in the head are able to grip a tool; and said bulbous end having an outer part terminating in a point for ease of insertion of said trocar button into an aperture.

7. A trocar button according to claim 6 and comprising:

a screw thread on the on the outside surface of said conical body;

that part of the cavity in said head comprising a second set of two spaced apart opposed walls defining a second groove which extends into the conical body;

in said second set, the distance between said two opposed walls in the head being less than the distance between said two opposed walls in the conical body so that said two opposed walls in the head are able to grip a tool; and said neck having an exterior surface;

said neck housing part of said cavity and a wall between said exterior surface and said cavity; and in said neck said wall is thin between said exterior surface and said cavity to allow easy separation of said bulbous end and said conical body.

8. A combination of a trocar button and a tool for manipulating the trocar button and comprising:

said trocar button comprising:

a head;

a conical body connecting with said head and said conical body having a larger part and a smaller part;

a bulbous end;

a neck connecting with said conical body and with said bulbous end and being of a lesser dimension than said bulbous end and said neck having an exterior surface;

said larger part of said conical body connecting with said head;

a cavity in said head, said conical body and in said bulbous end;

part of said cavity in said head comprising a first set of two spaced apart opposed walls defining a first groove which extends into the conical body;

a first distance, in said first set, between said two spaced apart opposed walls in the head being less than the distance between said two opposed walls in the conical body so that said two opposed walls in the head are able to grip a tool;

part of said cavity in said head comprising a second set of two spaced apart opposed walls defining a second groove which extends into the conical body;

a second distance, in said second set, between said two opposed walls in the head being less than the distance between said two opposed walls in the conical body so that said two opposed walls in the head are able to grip a tool;

said tool comprising:

a projection means;

the width of said projection means being greater than said first distance necessitating the forcing of said projection means between said two opposed walls in said first set so that said two opposed walls in said head are able to grip said tool;

said combination comprising:

said projection means being positioned between said two opposed walls in said first set.

9. A combination according to claim 8 and comprising:

a screw thread on the outside surface of said conical body;

said neck housing part of said cavity and a wall between said exterior surface and said cavity; and in said neck said wall is thin between said exterior surface and said cavity to allow easy separation of said bulbous end and said conical body.

10. A combination of a trocar button and a tool for manipulating the trocar button and comprising:

said trocar button comprising:

a head;

a conical body connecting with said head having a larger part, and a smaller part, and an outside surface a bulbous end;

a neck connecting with said conical body and with said bulbous end and being of a lesser dimension than said bulbous end and said neck having an exterior surface;

the larger part of said conical body connecting with said head;

a cavity in said head, said conical body and in said bulbous end;

part of said cavity in said head comprising a first set of two spaced apart opposed walls defining a first groove which extends into the conical body;

a first distance, in said first set, between said two spaced apart opposed walls in the head being less then the distance between said two opposed walls in the conical body so that said two opposed walls in the head are able to grip a tool;

part of said cavity in said head comprising a second set of two spaced apart opposed walls defining a second groove which extends into the conical body;

a second distance, in said second set, between said two opposed walls in the head being less than the distance between said two opposed walls in the conical body so that said two opposed walls in the head are able to grip a tool;

of said bulbous end having an outer part terminating in point for ease of insertion of said trocar button into an aperture;

said tool comprising:

a projection means;

the width of said projection means being greater than said first distance necessitating the forcing of said projection means between said two opposed walls in said first set so that said two opposed walls in said head are able to grip said tool;

said combination comprising:

said projection means being positioned between said two opposed walls in said first set.

11. A combination according to claim 10 and comprising:

a screw thread on the outside surface of said conical body;

said neck housing part of said cavity and a wall between said exterior surface and said cavity; and in said neck said wall is thin between said exterior surface and said cavity to allow easy separation of said bulbous end and said conical body.

* * * * *